US006462235B1

(12) United States Patent
Thiele et al.

(10) Patent No.: US 6,462,235 B1
(45) Date of Patent: Oct. 8, 2002

(54) PROCESS FOR PRODUCTION OF OXIMES COCATALYZED BY AMMONIUM SALTS OR SUBSTITUTED AMMONIUM SALTS

(75) Inventors: Georg Friedrich Thiele, Hanau; Thomas Schiffer, Haltern; Georg Oenbrink, Dülmen, all of (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/989,079

(22) Filed: Nov. 21, 2001

(30) Foreign Application Priority Data

Jan. 26, 2001 (DE) .......................... 101 03 581

(51) Int. Cl.⁷ ..................... C07C 249/06; C07C 249/08
(52) U.S. Cl. ....................... 564/253; 564/259
(58) Field of Search .................. 564/253, 259

(56) References Cited

U.S. PATENT DOCUMENTS 4,745,221 A    5/1988  Roffia et al.
4,794,198 A   12/1988  Roffia et al.
4,968,842 A * 11/1990  Padovan et al. ............ 564/253
5,041,652 A    8/1991  Padovan et al.
5,498,793 A    3/1996  Mantegazza et al.

FOREIGN PATENT DOCUMENTS

| DE | 19521011 A1 | 12/1995 |
| EP | 0208311 A2 | 1/1987 |
| EP | 0267362 A1 | 5/1988 |
| EP | 0299430 A1 | 1/1989 |
| EP | 0 690 045 A1 | 1/1996 |
| JP | 2000-72738 | 3/2000 |
| JP | 98-247281 | 7/2000 |

* cited by examiner

Primary Examiner—Brian J. Davis
(74) Attorney, Agent, or Firm—Oblon, Spivak, McClelland, Maier & Neustadt, P.C.

(57) ABSTRACT

Oximes are produced in high yields and with high selectivity by reacting aldehydes or ketones with hydrogen peroxide and ammonia in the presence of a heterogeneous catalyst and an ammonium salt or substituted ammonium salt. The heterogeneous catalyst is synthesized on the basis of titanium, silicon and oxygen. Optionally, a Lewis-acid and/or Brønsted-acid cocatalyst can be present.

24 Claims, No Drawings

PROCESS FOR PRODUCTION OF OXIMES COCATALYZED BY AMMONIUM SALTS OR SUBSTITUTED AMMONIUM SALTS

BACKGROUND OF THE INVENTION

1. Field of the Invention

The present invention relates to a catalytic process for producing oximes by reacting aldehydes or ketones with hydrogen peroxide and ammonia in the presence of a heterogeneous catalyst and an ammonium salt or a substituted ammonium salt.

2. Discussion of the Background

European patent applications EP-A-0 208 311, EP-A-0 267 362 and EP-A-0 299 430, as well as U.S. Pat. No. 4,794,198, describe the preparation and activation of a catalyst based on titanium, silicon and oxygen as well as its use for synthesizing oximes from aldehydes or ketones such as cyclohexanone by reaction with hydrogen peroxide and ammonia. This reaction is a so-called ammoximation. The catalysts usually exhibit a ratio of silicon: titanium of greater than 30. A typical agent is titanium silicalite TS1.

The synthesis of small aliphatic and cycloaliphatic oximes based on ketones with up to 6 carbon atoms, such as cyclopentanone and cyclohexanone, provides good results using titanium silicalite catalysts prepared and activated according to the above-mentioned documents. However, the results are clearly poorer in the case of larger or sterically higher-quality carbonyl compounds, such as acetophenone or cyclododecanone. In particular, the reaction rates, conversion of the carbonyl compounds and the yield with respect to hydrogen peroxide ($H_2O_2$ used for ammoximation: $H_2O_2$ necessary for total quantity×100%) are unsatisfactory.

Conversion rates of over 90% with a peroxide loss of less than 10% are achieved in the case of cyclohexanone as shown in Examples 22 and 24 of EP-A-0 267 362. However, conversion rates of only 50.8% with a peroxide loss of 48.9% are achieved with acetophenone under comparable reaction conditions. Conversion of cyclododecanone is claimed in the above-mentioned application, yet no concrete example of conversion and peroxide loss is given.

The clearly poorer yields with large or sterically high-quality carbonyl compounds can be attributed to, inter alia, the fact that large carbonyl compounds such as cyclododecanone (CDON) can either not penetrate the pores of the titanium silicalite catalyst at all, or, if they can penetrate, then only slowly. This can effectively result in a spatial separation of the partial steps of hydroxyl amine development (1) and oximation of the ketone (2), shown for the example for cyclododecanone (CDON) in the following reaction equations.

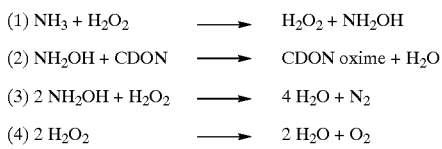
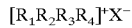

If the formed hydroxyl amine is not converted immediately or fully with the respective carbonyl compound, different secondary reactions increasingly occur, such as further oxidation of the hydroxyl amine with available hydrogen peroxide, represented formally as stoichiometric equation (3) above.

For the sake of completeness, another secondary reaction affecting peroxide selectivity is pointed out, namely the base-catalyzed or metal-catalyzed decomposition of hydrogen peroxide according to equation (4).

In German patent application DE 195 21 011 A1 (corresponding to U.S. Pat. No. 5,498,793) Enichem claims an amorphous silicon dioxide as a cocatalyst for ammoximation of acetophenone and cyclododecanone. With the addition of amorphous silicon dioxide conversion with cyclododecanone increases after an 8-hour reaction period to 85.5% or 85.2% (DE 195 21 011 A1, Examples 5 and 6), as compared to 76.6% without a cocatalyst. The peroxide yield simultaneously increases from 65.8% to 71.4% or 72.3%. The method described by Enichem results in a moderate improvement in conversion and peroxide yield, but the reaction method as described presents several disadvantages which show an industrial-scale application to be uneconomical.

The quantity of catalyst and cocatalyst in relation to the ketone is very high in the examples with each up to 25% by weight in the trials using cyclododecanone. Despite the high catalyst concentration, the conversion rate is minimal and the reaction is slow. The oxime yield is still far from reaching complete conversion, even after a total reaction time of 8 hours.

Secondary reactions according to partial steps (3) and (4) lower the space-time yield of the ammoximation, and they have an especially negative effect on peroxide selectivity. In the ammoximation of CDON without a cocatalyst, in some cases the peroxide selectivity rate is below 50%. However, with CDON it can be increased to approximately 60–70% using various cocatalysts, as described in German patent application P 100 47 435.7. However, this is still unsatisfactory for an industrial-scale process.

SUMMARY OF THE INVENTION

An object of the present invention is therefore to provide a process for ammoximation, in particular, of larger and sterically high-quality carbonyl compounds to give oximes with high peroxide selectivity, high conversion of the carbonyl compounds and high space-time yield.

Surprisingly, it was found that the above-mentioned problems are solved if an ammonium salt or a substituted ammonium salt is present during the reaction.

Accordingly, the above and other objects of the present invention have been achieved by a process for producing an oxime, comprising:

reacting a carbonyl compound in the liquid phase with hydrogen peroxide and ammonia in the presence of a) a heterogeneous catalyst and b) an ammonium salt, a substituted ammonium salt or a mixture of an ammonium salt and a substituted ammonium salt;

wherein said heterogeneous catalyst comprises titanium, silicon and oxygen;

wherein said ammonium salt or said substituted ammonium salt is represented by formula:

$$[R_1R_2R_3R_4]^+X^-$$

wherein $R^1$, $R_2$, $R_3$ and $R_4$ each independently of one another represent hydrogen, an aliphatic, unbranched or branched alkyl radical having 1 to 20 carbon atoms, a cycloaliphatic radical having 3 to 12 carbon atoms, or an aromatic radical having a total of 6 to 12 carbon atoms; and wherein $X^-$ represents an anion.

DETAILED DESCRIPTION OF THE INVENTION

The present invention accordingly relates to a process for producing oximes by reacting carbonyl compounds, in particular aldehydes or ketones, such as acetophenone, and cyclic ketones having 7 to 20 carbon atoms, such as cyclododecanone, in the liquid phase with hydrogen peroxide and ammonia in the presence of one or more heterogeneous catalysts and ammonium salts or substituted ammonium salts. Other constituents can be added optionally, such as, for example, acidic or neutral, inorganic or organic solids as cocatalysts and/or binders.

The heterogeneous catalyst is synthesized on the basis of titanium, silicon and oxygen. The catalyst is preferably a so-called titanium silicalite. The catalysts preferably have a micro-porous or meso-porous structure and preferably have a ratio of silicon: titanium of greater than 30. A preferred and particularly active agent is titanium silicalite TS1.

In addition to the titanium silicalite catalyst, other compounds which exhibit Lewis-acid and/or Brønsted-acid centers on the surface or in pores, can optionally be present as cocatalysts. Non-limiting, preferred examples of inorganic cocatalysts are aluminum oxides, in particular, acidic aluminum oxides, acidic activated alumosilicates, such as bentonite, montmorrilonite and kaolinite according to German patent application P 100 47 435.7, or amorphous silicon dioxide according to German patent application DE 195 21 011 A1 (Enichem). Non-limiting, preferred examples for cocatalysts synthesized on organic carrier materials are acidic and strongly acidic ion exchange resins such as Amberlyst 15 or Nafion NR 50 according to German patent application P 100 47 435.7. A functional group having Lewis-acid or Brønsted-acid properties can be physically adhered or chemically bonded to the carrier material.

As a solid material the catalyst and cocatalyst can be used both as a powder and as a molded body. The weight ratio of catalyst (preferably the above-mentioned titanium silicalite) and cocatalyst usually varies between 0.1:1 and 10:1. The solid cocatalyst preferably also assumes the function of the binder in the case of the molded body.

The ammonium ions or substituted ammonium ions, hereinafter designated as ammonium ions for the sake of simplicity, which have the effect of a cocatalyst according to the present invention, are homogeneously dissolved in the liquid phase. The following options are suitable for introducing the ammonium ions:

The ammonium ions can be dissolved in the solvent in the form of a suitable ammonium salt. In a discontinuous operation they are preferably added with the titanium catalyst to the reactor. In a continuous operation they are introduced to the reactor continuously with the carbonyl compound.

The ammonium ions can be first formed in the reactor, in that a suitable acid, which is immediately neutralized with the ammonia present in the reactor or with an amine to the corresponding ammonium salts, is added to the reaction mixture. A suitable derivative of the free acid can be added instead (an anhydride, for example), which forms ammonium ions or substituted ammonium ions with ammonia or an amine.

The ammonium ions or substituted ammonium ions are represented by formula $[R^1R_2R_3R_4]^+X^-$, wherein $R^1$, $R_2$, $R_3$, $R_4$ independently of one another represent hydrogen; an aliphatic, unbranched or branched alkyl radical having 1 to 20 carbon atoms, preferably 1 to 6 carbon atoms, e.g. a methyl-, ethyl-, propyl- or butyl-residue; a cycloaliphatic residue having 3 to 12 carbon atoms; or an aromatic residue having a total of 6 to 12 carbon atoms; and wherein $X^-$ represents an anion that is selected in such a way that the corresponding ammonium compound in the system is sufficiently soluble. In the case of the alkyl chains, the substituted ammonium compounds also guarantee adequate solubility in less polar solvents.

As Examples 1 to 4 demonstrate, the ammonium ions are required not stoichiometrically, but in catalytic quantities.

As a rule, a very small concentration of ammonium ions is latently present in the reaction mixture. This concentration can be, for example, between 0.1 and 1000 ppm. It results from the fact that commercially available hydrogen peroxide is generally stabilized by orthophosphoric or pyrophosphoric acid. With the presence of ammonia, ammonium ions form in small concentrations by neutralization.

Japanese patent application JP 98-247281 (Mitsubishi Gas Chemical Co.) claims a peroxide stabilizer content of 1 to 1000 ppm relative to the quantity of hydrogen peroxide in ammoximation.

In the above-mentioned example of the British abstract of JP 98-247281 hydrogen peroxide is used with 30 ppm of orthophosphoric acid relative to $H_2O_2$. A corresponding hydrogen peroxide also with 30 ppm orthophosphoric acid as a stabilizer was also used in the following Examples 1 to 4 and 6 as well as in Comparative Examples 5 and 7 of the present application.

Examples 1 to 7 have in the reaction mixture an ammonium concentration of at most 0.4 ppm due to the phosphoric acid that is present, assuming that the phosphoric acid is reacted fully with three equivalents of ammonia to give ammonium phosphate $(NH_4)_3PO_4$.

An ammonium ion content of at most 14 ppm in the reaction mixture results using the operation outlined in the Examples, if the maximum value of 1000 ppm phosphoric acid relative to $H_2O_2$ as claimed in JP 98-247281 is used as stabilizer for the hydrogen peroxide. 1 s In the experiments of the present invention it was clearly shown that the concentration of ammonium ions introduced by a peroxide stabilizer is inadequate for catalysis of ammoximation. Thus, additional ammonium ions must be introduced to the reaction mixture by one of the above-described methods. In addition, it is important for high conversion rates of the aldehyde or ketone and for the peroxide selectivity that a sufficiently high ammonium ion concentration is present at the beginning of the reaction. This ammonium concentration is not adjusted during the course of the reaction by the addition of $H_2O_2$. The term conversion refers to a reaction. The conversion rate refers to the amount of starting material such as an aldehyde or a ketone that has reacted to give the oxime.

An ammonium concentration of at least 100 ppm, preferably at least 250 ppm, and particularly preferably at least 500 ppm, is required in the reaction mixture for a noticeable catalytic effect. The ammonium concentration is calculated as $(NR_1R_2R_3R_4)^+$.

The upper limit of the ammonium concentration results, on the one hand, from the solubility of the salt in the respective solvent, and on the other hand from the fact that from a certain level of ammonium ion concentration no further improvement in the conversion rate or peroxide selectivity is achieved. Depending on the salt and solvent the ammonium concentration can amount to as much as 20% by weight.

Ammonium salts that are moderately to very soluble in a solvent are preferred. Particularly preferred are, for example, halogenides, nitrate and phosphate, and most preferred are ammonium salts of organic carboxylic acids and their mixtures. Non-limiting, preferred examples of salts of organic carboxylic acids are ammonium formate, ammonium acetate, ammonium propionate, ammonium oxalate and ammonium malonate.

Preferred solvents can be compounds which are stable when contacted with hydrogen peroxide and ammonia and which exhibit adequate solubility, both, for the carbonyl function and the formed oxime as well as for the ammonium salt. Short-chain aliphatic alcohols such as methanol, ethanol, n-propanol, n-butanol, isobutanol, tert.-butanol and tert.-amylalcohol are preferred as solvents. Methanol, ethanol and tert.-butanol are particularly preferred for the reaction with CDON.

Ammonia is required as a reagent during ammoximation and is present in an excess. The ammonia is introduced as concentrated, preferably aqueous solution ($\geq 20\%$ by weight) or preferably as dry gas. The reaction runs in the basic medium by means of the ammonia excess. The excess of ammonia is between 0.5 to 200% by weight. The excess of ammonia is preferably 10%, more preferably 50% and most preferably 100%.

Hydrogen peroxide is used as a 0.1 to 85% by weight solution, preferably as an aqueous solution. Concentrated aqueous solutions with $\geq 30\%$ by weight are preferred.

One goal in selecting the concentrations of the ammonia solution and hydrogen peroxide solution is to keep the proportion of water in the solvent as low as possible, because water lowers the solubility of the carbonyl compounds, in particular oximes.

The reaction according to the present invention runs highly selectively with respect to ammoximation of carbonyl compound. Oxime selectivity rates of more than 99% are achieved with cyclododecanone and high conversion rates of >99.5% are achieved according to the gas chromatogram (GC). If, for example, technically pure cyclododecanone is used, traces of cycododecane and cyclododecanol which were already present in the cyclododecanone as an impurity can be detected as secondary products in the GC. With water contents in the solvent of less than 1%, traces of cyclododecanonimine could be detected as an intermediate/secondary product which is reacted again reversibly to the ketone during reaction and then converted to the oxime.

The reaction temperature of ammoximation is between 20° C. and 150° C., preferably between 50° C. and 120° C. and particularly preferably between 60° C. and 100° C. The reaction temperature includes all values and subvalues therebetween, especially including 30, 40, 50, 60, 70, 80, 90, 100, 110, 120, 130 and 140° C.

The reactor is operated at either normal pressure, that is the vapor pressure of the respective solvent at the selected reaction temperature, or at a slight overpressure, preferably between 1 bar and 10 bar. The pressure includes all values and subvalues therebetween, especially including 2, 3, 4, 5, 6, 7, 8 and 9 bar. The excess pressure can be adjusted by adding ammonia or an inert gas. If the reactor is closed, the pressure rises through the formation of gaseous decomposition products in secondary reactions (especially nitrogen) during the reaction. The reactor is advantageously operated in an isobaric manner, so that gaseous decomposition products can escape by way of a moderate waste gas flow controlled with a bubble gauge. Used ammonia is returned to the reactor, if required.

Both, the carbonyl compound and hydrogen peroxide, can be added discontinuously or continuously. A slight excess of peroxide solution is required for complete alkanal/alkanone conversion. The excess can be minimized by appropriate control of the reaction and the ammonium concentration of the catalyst system according to the present invention. It is preferred to either add the carbonyl compound at the beginning of the reaction or to meter it in equimolar quantities along with the hydrogen peroxide and to add the required surplus of peroxide according to the rate of consumption after all the carbonyl has been added.

Having generally described this invention, a further understanding can be obtained by reference to certain specific examples which are provided herein for purposes of illustration only, and are not intended to be limiting unless otherwise specified.

EXAMPLES

To ensure precisely identical reaction conditions fresh catalyst (titanium silicalite TS1, Degussa-Hüls AG) from the same batch was used in each of the examples. An aqueous solution of hydrogen peroxide (50% by weight with 30 ppm phosphoric acid as stabilizer) was used for all trials. There was no additional activation of the catalyst prior to reaction. The catalyst was separated off after the reaction at 75° C. by way of a pressure filter and could thus be recycled with high residual activity.

Example 1

5.25 g (68 mmol) of ammonium acetate dissolved in 300 ml (243 g) ethanol were placed in a 1.6-litre heatable glass pressure reactor (Büchi autoclave), which had been flushed with nitrogen, with magnetic coupling, gas distribution stirrer (500 rpm) and a pressure regulator. 5.0 g of catalyst (TS1, Degussa-Hüls) were suspended therein. At 40° C. 62.7 g (344 mmol) of cyclododecanone (CDON) in 251 g of ethanol were added. The reactor was heated to 80° C. and the pressure was reduced to 0.1 bar, after which ammonia gas was slowly pressurized to a pressure of 1.6 bar. Approximately 13 g (approx. 765 mmol) of ammonia were added. This corresponded to approximately 2.2 equivalents relative to cyclododecanone.

During the reaction the pressure was kept constant by means of a slight waste gas flow and the escaped ammonia gas was replaced (~0.4 g/h). 24.5 ml (28.56 g) (0.41 ml/min) of a 50% hydrogen peroxide solution (corresponding to 430 mmol [14.62 g] $H_2O_2$) were added via a pump over a period of 60 minutes. After the peroxide was added, the reaction mixture was left to react further for another 60 minutes.

During the reaction, CDON conversion was tracked via gas chromatography and hydrogen peroxide was determined iodometrically. After 120 minutes, the CDON conversion was 99.95%; 426 mmol of $H_2O_2$ were consumed, corresponding to a peroxide selectivity rate of 80.6%, relative to converted CDON.

Further results are itemized in Tables 1 to 3.

Example 2

Example 2 was carried out according to Example 1. 22.0 ml (0.37 ml/min) of a 50% by weight hydrogen peroxide solution (corresponding to 385 mmol [13.09 g] $H_2O_2$) were added via a pump over a period of 60 minutes. After the peroxide was added the reaction mixture was left to react further for another 60 minutes.

After 120 minutes the CDON conversion was 99.90%; 384 mmol of $H_2O_2$ were consumed, corresponding to a peroxide selectivity rate of 89.2%. Further results are itemized in Tables 1 to 3.

Example 3

Example 3 was repeated according to Example 2 with 2.63 g of ammonium acetate. 22.0 ml (0.37 ml/min) of a 50% by weight hydrogen peroxide solution (corresponding to 385 mmol [13.09 g] $H_2O_2$) were added via a pump over a period of 60 minutes. After 120 minutes the CDON conversion was 99.91%; 382 mmol of $H_2O_2$ were consumed, corresponding to a peroxide selectivity rate of 90.0%. Further results are itemized in Tables 1 to 3.

Example 4

Example 4 was repeated according to Example 2 with 0.53 g of ammonium acetate. 22.0 ml (0.37 ml/min) of a 50% by weight hydrogen peroxide solution (corresponding to 385 mmol [13.09 g] $H_2O_2$) were added via a pump over a period of 60 minutes. After 120 minutes the CDON conversion was 79.42%; 371 mmol of $H_2O_2$ were consumed, corresponding to a peroxide selectivity rate of 73.5%. Further results are itemized in Tables 1 to 3.

Example 5: (Comparative example)

Example 5 was repeated according to Examples 2 and 3, but without ammonium acetate.

22.0 ml (0.37 ml/min) of a 50% by weight hydrogen peroxide solution (corresponding to 385 mmol [13.09 g] $H_2O_2$) were added via a pump over a period of 60 minutes. After the peroxide was added the reaction mixture was left to react further for another 120 minutes.

Conversion was tracked during the reaction via gas chromatography, and hydrogen peroxide was determined iodometrically. After 120 minutes the CDON conversion was 32.80%, and after 180 minutes 33.31%; 378 mmol of $H_2O_2$ were consumed, corresponding to a peroxide selectivity rate of 30.3%. Further results are itemized in Tables 1 to 3.

TABLE 1

CDON Conversion During Reaction Time

| Example No. (Salt) | 30 min [%] | 60 min [%] | 120 min [%] | 180 min [%] |
| --- | --- | --- | --- | --- |
| 1 (5.25 g NH₄OAC) | 58.51 | 99.42 | 99.95 | — |
| 2 (5.25 g NH₄OAc) | 51.04 | 98.34 | 99.90 | — |
| 3 (2.63 g NH₄OAc) | 60.26 | 90.10 | 99.91 | — |
| 4 (0.53 g NH₄OAc) | 42.50 | 74.50 | 79.42 | — |
| 5 (without) | 12.10 | 28.85 | 32.80 | 33.31 |

TABLE 2

Conversion Rate

| Example No. (Salt) | Conversion rate after 60 min [mg oxime/(g TS 1 *min)] |
| --- | --- |
| 1 (5.25 g NH₄OAc) | 207.8 |
| 2 (5.25 g NH₄OAc) | 205.5 |
| 3 (2.63 g NH₄OAc) | 188.3 |
| 4 (0.53 g NH₄OAc) | 155.7 |
| 5 (without) | 60.3 |

TABLE 3

Converted Peroxide/Peroxide Selectivity (%)

| Example No. (Salt) | 120 (180*) min. consumed $H_2O_2$ [mmol] | $H_2O_2$ selectivity or converted CDON |
| --- | --- | --- |
| 1 (5.25 g NH₄OAc) | 426 | 80.6% |

TABLE 3-continued

Converted Peroxide/Peroxide Selectivity (%)

| Example No. (Salt) | 120 (180*) min. consumed $H_2O_2$ [mmol] | $H_2O_2$ selectivity or converted CDON |
| --- | --- | --- |
| 2 (5.25 g NH₄OAc) | 384 | 89.2% |
| 3 (2.63 g NH₄OAc) | 382 | 90.0% |
| 4 (0.53 g NH₄OAc) | 371 | 73.5% |
| 5 (without) | 378 | 30.3% |

Examples 6 and 7 show conversion with acetophenone. The parameter adjustments optimized for CDON were assumed.

Example 6

Example 6 was repeated according to Example 1.

41.33 g (344 mmol) of acetophenone were used instead of cyclododecanone. 24.5 ml (0.41 ml/min) of a 50% by weight hydrogen peroxide solution (corresponding to 430 mmol [14.62 g] $H_2O_2$) were added via a pump over a period of 60 minutes. After the peroxide was added the reaction mixture was left to react further for another 60 minutes.

After 120 minutes the acetophenone conversion was 84.29%; 416 mmol of $H_2O_2$ were consumed, corresponding to a peroxide selectivity rate of 69.7%.

Example 7 (comparative example)

Example 7 was repeated according to Example 6, but without the addition of ammonium acetate.

24.5 ml (0.41 ml/min) of a 50% by weight aqueous hydrogen peroxide solution with 30 ppm orthophosphoric acid as stabilizer (corresponding to 430 mmol [14.62 g] $H_2O_2$) were added via a pump over a period of 60 minutes. After the peroxide was added the reaction mixture was left to react further for another 60 minutes.

After 120 minutes the acetophenone conversion was 13.6%; 406 mmol of $H_2O_2$ were consumed, corresponding to a peroxide selectivity rate of 11.5%.

Example 8

The experimental setup from Example 1 was supplemented by a fixed-bed reactor with circulation pump (600 ml/min). As a fixed-bed catalyst 50 g of molded bodies (1 mm diameter granulate) were used; these were manufactured in the extruder from 80% by weight of titanium silicalite TS1 (Degussa-Hüls AG) and 20% by weight of aluminum oxide Pural SB as an acidic cocatalyst. The reaction was run as per Example 1 under constant pressure (1.6 bar) and 80° C.

608 g of a 12% by weight solution of cyclododecanone (73 g, 400 mmol) in ethanol were added and 5.8 g of ammonium acetate were dissolved therein. This corresponded to an ammonium ion concentration of 0.1 mol/l in the reaction mixture.

25.1 ml (0.139 ml/min) of a 50% by weight hydrogen peroxide solution (corresponding to 440 mmol [14.96 g] $H_2O_2$) were added over a period of 3 hours. After the peroxide was added the reaction mixture was left to react further for another hour. After 240 minutes the CDON conversion rate was 97.15%; 435 mmol of $H_2O_2$ were consumed, corresponding to a peroxide selectivity rate of 89.3%.

German patent application 10103581.0, filed Jan. 26, 2001, is incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A process for producing an oxime, comprising:
reacting a carbonyl compound in the liquid phase with hydrogen peroxide and ammonia in the presence of a) a heterogeneous catalyst and b) an ammonium salt, a substituted ammonium salt or a mixture of an ammonium salt and a substituted ammonium salt;
wherein said heterogeneous catalyst comprises titanium, silicon and oxygen; wherein said ammonium salt or said substituted ammonium salt is represented by formula:

wherein $R_1$, $R_2$, $R_3$ and $R_4$ each independently of one another are hydrogen, an aliphatic, unbranched or branched alkyl radical having 1 to 20 carbon atoms, a cycloaliphatic radical having 3 to 12 carbon atoms, or an aromatic radical having a total of 6 to 12 carbon atoms; and
wherein $X^-$ is an anion.

2. The process as claimed in claim 1, wherein a concentration of an ammonium ion or a substituted ammonium ion is 100 ppm to 20% by weight; and
wherein said ammonium salt or said substituted ammonium salt is homogeneously dissolved in said liquid phase.

3. The process as claimed in claim 1, wherein a concentration of an ammonium ion or a substituted ammonium ion is 500 ppm to 20% by weight; and
wherein said ammonium salt or said substituted ammonium salt is homogeneously dissolved in said liquid phase.

4. The process as claimed in claim 1, wherein $R_1$, $R_2$, $R_3$ and $R_4$ are hydrogen.

5. The process as claimed in claim 1, wherein $X^-$ is a halogenide, a nitrate ion, a phosphate ion or an anion of a carboxylic acid.

6. The process as claimed in claim 5, wherein said ammonium salt is selected from the group consisting of ammonium formate, ammonium acetate, ammonium propionate, ammonium oxalate, ammonium malonate and mixtures thereof.

7. The process as claimed in claim 1, wherein a cocatalyst comprising an acidic solid which contains an inorganic or organic carrier material is present;
wherein either said carrier material itself has Lewis-acid or Bronsted-acid properties or a functional group having Lewis-acid or Brønsted-acid properties is physically adhered or chemically bonded to said carrier material.

8. The process as claimed in claim 1, wherein said heterogeneous catalyst is a titanium silicalite.

9. The process as claimed in claim 1, wherein said heterogenous catalyst is titanium silicalite TS1.

10. The process as claimed in claim 1, wherein an ammonium ion or a substituted ammonium ion is introduced by dissolving an ammonium salt in said liquid phase.

11. The process as claimed in claim 1, wherein an ammonium ion or a substituted ammonium ion is introduced in said liquid phase by neutralizing a free acid or a derivative thereof with ammonia.

12. The process as claimed in claim 1, wherein said carbonyl compound is acetophenone or a cyclic ketone having 7 to 20 carbon atoms.

13. The process as claimed in claim 1, wherein said carbonyl compound is cyclododecanone.

14. The process as claimed in claim 1, wherein an alcohol that is fully or partially miscible with water is added as a solvent.

15. The process as claimed in claim 1, wherein a reaction temperature is between 20° C. and 150° C.

16. The process as claimed in claim 1 wherein a pressure during said reacting is 1 bar to 10 bar.

17. The process as claimed in claim 1, wherein said catalyst has a micro-porous or a meso-porous structure.

18. The process as claimed in claim 1, wherein a ratio of silicon to titanium in said catalyst is greater than 30.

19. The process as claimed in claim 7, wherein said cocatalyst contains an aluminum oxide.

20. The process as claimed in claim 7, wherein said catalyst or said cocatalyst is used in the form of a powder or a molded body.

21. The process as claimed in claim 7, wherein a weight ratio of said catalyst to said cocatalyst is between 0.1:1 and 10:1.

22. The process as claimed in claim 1, wherein said ammonia is present in an excess of at least 50%.

23. The process as claimed in claim 1, wherein said ammonia is present in an excess of between 0.5 to 200% by weight.

24. The process as claimed in claim 1, wherein said hydrogen peroxide is a 0.1 to 85% by weight solution.

* * * * *

UNITED STATES PATENT AND TRADEMARK OFFICE
CERTIFICATE OF CORRECTION

PATENT NO. : 6,462,235 B1
DATED : October 8, 2002
INVENTOR(S) : Georg Friedrich Thiele et al.

It is certified that error appears in the above-identified patent and that said Letters Patent is hereby corrected as shown below:

Column 2,
Line 54, the formula "$[R_1R_2R_3R_4]^+X^-$" should read -- $[NR_1R_2R_3R_4]^+X^-$ --.

Column 3,
Line 58, "ammonium ions or substituted ammonium ions" should read -- ammonium ions and salts or substituted ammonium ions and salts --;

Line 59, "$[R^1R_2R_3R_4]^+X^-$,", should read -- $[NR_1R_2R_3R_4]^+X^-$ --.

Column 4,
Line 51, "$(NR_1R_2R_3R_4)^+$" should read -- $[NR_1R_2R_3R_4]^+$ --.

Column 9,
Line 20, the formula "$[R_1R_2R_3R_4]^+X^-$" should read -- $[NR_1R_2R_3R_4]^+X^-$ --.

Signed and Sealed this

Eighth Day of June, 2004

JON W. DUDAS
*Acting Director of the United States Patent and Trademark Office*